US012357847B2

(12) United States Patent
Kim et al.

(10) Patent No.: US 12,357,847 B2
(45) Date of Patent: Jul. 15, 2025

(54) ULTRASONIC WAVE GENERATING CARTRIDGE, ULTRASONIC WAVE GENERATING DEVICE, ULTRASONIC WAVE GENERATING HANDPIECE, AND METHOD FOR SENSING POSITION OF ULTRASONIC WAVE GENERATING UNIT USING SAME

(71) Applicant: JEISYS MEDICAL INC., Seoul (KR)

(72) Inventors: Kyun Tae Kim, Seoul (KR); Hyun Jin Kim, Seoul (KR); Dong Hwan Kang, Seoul (KR); Won Ju Yi, Seoul (KR)

(73) Assignee: Jeisys Medical Inc., Seoul (KR)

( * ) Notice: Subject to any disclaimer, the term of this patent is extended or adjusted under 35 U.S.C. 154(b) by 82 days.

(21) Appl. No.: 18/328,509

(22) Filed: Jun. 2, 2023

(65) Prior Publication Data

US 2023/0310902 A1    Oct. 5, 2023

Related U.S. Application Data

(63) Continuation of application No. PCT/KR2021/016886, filed on Nov. 17, 2021.

(30) Foreign Application Priority Data

Dec. 7, 2020   (KR) .................. 10-2020-0169108

(51) Int. Cl.
*A61N 7/00* (2006.01)

(52) U.S. Cl.
CPC ........ *A61N 7/00* (2013.01); *A61N 2007/0008* (2013.01); *A61N 2007/0091* (2013.01)

(58) Field of Classification Search
None
See application file for complete search history.

(56) References Cited

U.S. PATENT DOCUMENTS

| 10,856,842 | B2 | 12/2020 | Park et al. |
| 2016/0038771 | A1* | 2/2016 | Jung ........................ A61N 7/02 601/3 |
| 2017/0303895 | A1 | 10/2017 | Park et al. |

(Continued)

FOREIGN PATENT DOCUMENTS

| KR | 10-2013-0019764 A | 2/2013 |
| KR | 10-2015-0115432 A | 10/2015 |

(Continued)

OTHER PUBLICATIONS

International Search Report issued in PCT/KR2021/016886; mailed Feb. 28, 2022.

(Continued)

*Primary Examiner* — Joseph M Santos Rodriguez
*Assistant Examiner* — Tommy T Ly
(74) *Attorney, Agent, or Firm* — Leydig, Voit & Mayer, Ltd.

(57) ABSTRACT

The present invention relates to an ultrasonic wave generating cartridge which comprises: a cartridge housing; an ultrasonic wave generating unit which is disposed so as to be able to move in a reciprocating manner in the cartridge housing; and a position detection unit which can detect the real-time position of the ultrasonic wave generating unit by sending a transmission signal to the movement path of the ultrasonic wave generating unit.

19 Claims, 11 Drawing Sheets

(56) References Cited

U.S. PATENT DOCUMENTS

2019/0366129 A1    12/2019  Park et al.
2022/0401760 A1*   12/2022  Lee .......................... A61N 7/02

FOREIGN PATENT DOCUMENTS

| KR | 10-2016-0103760 A |   | 9/2016  |
|----|-------------------|---|---------|
| KR | 10-2017-0085018 A |   | 7/2017  |
| KR | 10-1756618 B1     |   | 7/2017  |
| KR | 10-2018-0015095 A |   | 2/2018  |
| KR | 10-2018-0136426 A |   | 12/2018 |
| KR | 20180136426 A     | * | 12/2018 |

OTHER PUBLICATIONS

A Notice of Office Action mailed by the Korean Intellectual Property Office on Oct. 13, 2022, which corresponds to Korean Patent Application No. 10-2020-0169108 with English language translation.

* cited by examiner

ULTRASONIC WAVE GENERATING CARTRIDGE, ULTRASONIC WAVE GENERATING DEVICE, ULTRASONIC WAVE GENERATING HANDPIECE, AND METHOD FOR SENSING POSITION OF ULTRASONIC WAVE GENERATING UNIT USING SAME

CROSS-REFERENCE TO RELATED APPLICATIONS

The present application is a continuation of International Patent Application No. PCT/KR2021/016886, filed on Nov. 17, 2021, which is based upon and claims the benefit of priority to Korean Patent Application No. 10-2020-0169108 filed on Dec. 7, 2020. The disclosures of the above-listed applications are hereby incorporated by reference herein in their entirety.

BACKGROUND

Embodiments of the inventive concept described herein relate to a cartridge, a device, and a handpiece for generating ultrasonic waves, and a method for sensing a position of an ultrasonic wave generating unit using the same.

There is a layer of adipose tissue under the dermis and epidermis of the skin. Cellulite is more likely to be made in the subcutaneous fat layer, and has a unique characteristic when compared to another fat layer, because the cellulite may be organized into a specific chamber surrounded by strands of connected tissues. An excessively larger fat tissue may cause obesity, cellulite, sagging skin and wrinkles.

Subcutaneous fat, which occupies the most part of the adipose tissue, is divided into a shallow adipose layer and a deep adipose layer. Deep fat is positioned between the subcutaneous and fascia in the abdomen, waist hip, and thigh and forms a deep fat section. This deep fat layer clearly tends to be accumulated in the local area. Local fat accumulation produced with age increases in volume within the confined space due to the thinning of fibrous bulkheads and the deficits of the fibrous bulkheads. Accordingly, the local fat accumulation tends to pop up at the lower portion of the waist.

The skin expands convexly due to the excessive local concentration of fat, and in connection with undesirable skin contours, the shape of skin may be improved when the lipid-rich fat layer is removed.

Recently, a procedure using ultrasonic waves has been widely known as a non-invasive way to reduce a subcutaneous fat layer or fat tissue.

The ultrasonic wave, which refers to a wave having the frequency of 20 kHz or more, may be variously utilized in a medical field of not only diagnosing and treating an affected part, but also skin beauty.

In particular, an obesity treatment technology using High Intensity Focus Ultrasound (HIFU) was originally used for anti-cancer treatment by selectively solidifying internal organ tumors at higher temperature to destroy cancer cells. However, Solta Medical in the U.S. first developed equipment called Liposonix having the HIFU to treat abdominal obesity in the human body. As described above, the equipment employing the HIFU for the procedure is referred to as an ultrasonic wave generator.

The ultrasonic wave generator focuses HIFU, which is generated from an ultrasonic wave generating unit, onto a deep part of a skin to induce the fat coagulation necrosis without any damage to a skin surface, which is different from a laser and an RF equipment The necrotized fat cells are naturally removed by a repair mechanism of a damaged part of a human body.

To improve convenience when performing the procedure using the HIFU, there has been suggested a technique for moving the ultrasonic wave generating unit that generates the HIFU.

As described above, when the ultrasonic wave generating unit moves, it is significantly important to exactly sense the real-time position of the ultrasonic wave generating unit. This is because even if the final position of the ultrasonic wave generating unit is slightly out of the target position of the ultrasonic wave generating unit, the focus of the HIFU from the ultrasonic wave generating unit is out of the target position of the deep part of the skin.

However, it is difficult for a conventional ultrasonic wave generating unit to sense the position of the ultrasonic wave generating unit in real time.

SUMMARY

Embodiments of the inventive concept provide a cartridge, a device, and a handpiece for generating ultrasonic waves, capable of sensing a position of an ultrasonic wave generating unit in real time, and a method for sensing a position of an ultrasonic wave generating unit.

Objects to be solved by the inventive concept are not limited to the objects mentioned above, and other objects not mentioned will be clearly understood by those skilled in the art from the following description.

According to an embodiment of the inventive concept, the cartridge for generating the ultrasonic wave includes a cartridge housing, an ultrasonic wave generating unit provided in the cartridge housing to reciprocate, and a position sensing unit to sense a real-time position of the ultrasonic wave generating unit by transmitting a transmission signal to a movement path of the ultrasonic wave generating unit.

In addition, the position sensing unit may include a transmission unit to transmit the transmission signal, and a reception unit to receive the transmission signal.

Further, the position sensing unit may further include a reflection unit to reflect the transmission signal.

In addition, the transmission unit and the reception unit may be aligned in line with each other, or disposed to be opposed to each other.

In addition, the transmission unit may include at least one transmission unit, the reception unit may include at least one reception unit, and the at least one transmission unit and the at least one reception unit are disposed in line with each other or disposed to be opposed to each other along the movement path of the ultrasonic wave generating unit.

Further, the ultrasonic wave generating unit may include a target member to block the transmission signal while passing between the transmission unit and the reception unit, when the ultrasonic wave generating unit moves, and a transducer coupled to the target member.

In addition, when a sensing region is formed between the transmission unit and the reception unit, a distance between two sensing regions adjacent to each other may be less than a width in a moving direction of the target member Further, the target member may have at least one target slit allowing the transmission signal to pass through the at least one target slit.

In addition, the cartridge may include a guide shaft disposed in the cartridge housing, and the ultrasonic wave generating unit may include a slider to slide along the guide shaft, as the guide shaft passes through the slider, and a bushing provided on an inner circumferential surface of the slider.

Further, the bushing may have a polygonal shape.

In addition, the cartridge may further include a pair of bellows disposed to be spaced apart from each other in the moving direction of the target member, in the cartridge housing, and the ultrasonic wave generating unit may include a mounter interposed between the pair of bellows.

Further, an inserting protrusion may be formed to protrude from one of the bellows and the mounter, and a recess may be formed in the other one of the bellows and the mounter, such that the inserting protrusion is detachably coupled to the recess.

According to an embodiment of the inventive concept, a device for generating ultrasonic waves in which the cartridge for generating the ultrasonic wave is mounted in a handpiece.

According to an embodiment of the inventive concept, a handpiece for generating ultrasonic waves includes the handpiece, a cartridge housing detachably provided in the handpiece, an ultrasonic wave generating unit provided to reciprocate in the cartridge housing, and the handpiece may include a position sensing unit to sense a real-time position of the ultrasonic wave generating unit.

According to an embodiment of the inventive concept, a method for sensing a position of an ultrasonic wave generating unit using the cartridge for generating ultrasonic waves may include transmitting a transmission signal to a movement path of the ultrasonic wave generating unit, and sensing a real-time position of the ultrasonic wave generating unit based on the transmission signal.

In addition, a method for sensing a position of an ultrasonic wave generating unit using the handpiece for generating the ultrasonic wave may include transmitting a transmission signal to a movement path of the ultrasonic wave generating unit, and sensing a real-time position of the ultrasonic wave generating unit based on the transmission signal. Details of the inventive concept are included in the detailed description and drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
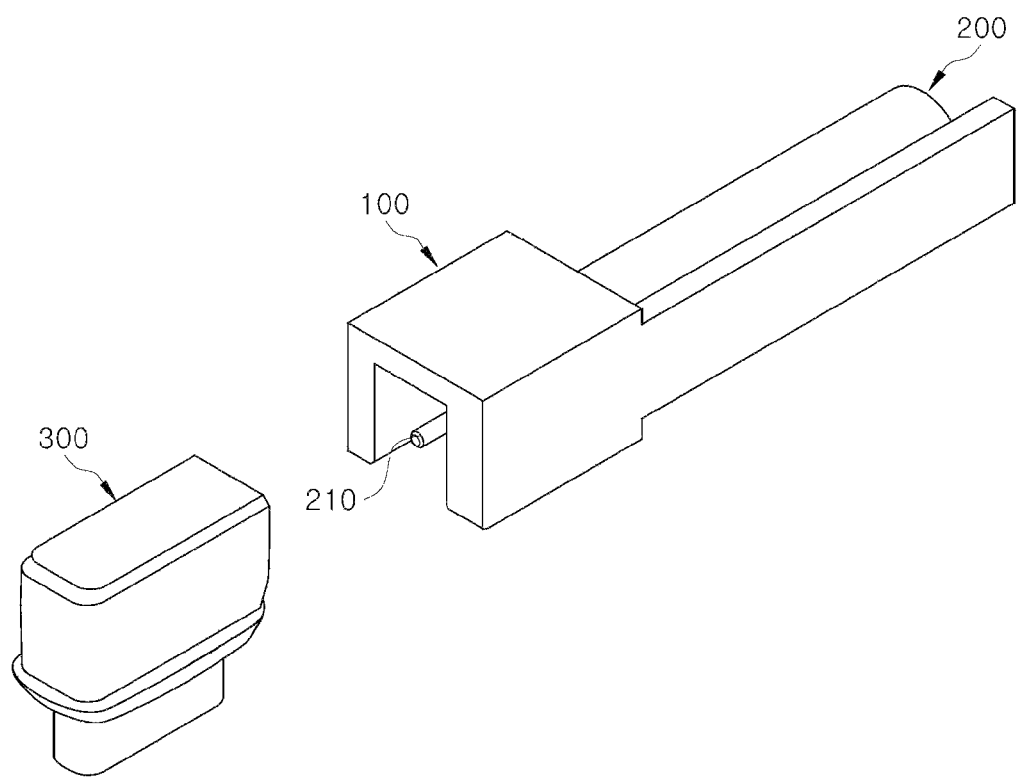
FIG. 1 is an exploded perspective view illustrating a device for generating ultrasonic waves, according to an embodiment of the inventive concept.

The above and other aspects, features and advantages of the inventive concept will become apparent from embodiments to be described in detail in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the scope of the inventive concept to those skilled in the art. The inventive concept may be defined by the scope of the claims.

The terms used herein are provided to describe embodiments, not intended to limit the inventive concept. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the relevant art and will not be interpreted in an idealized or overly formal detect unless expressly so defined herein.

Hereinafter, embodiments of the inventive concept will be described with reference to accompanying drawings.

Figure 2:
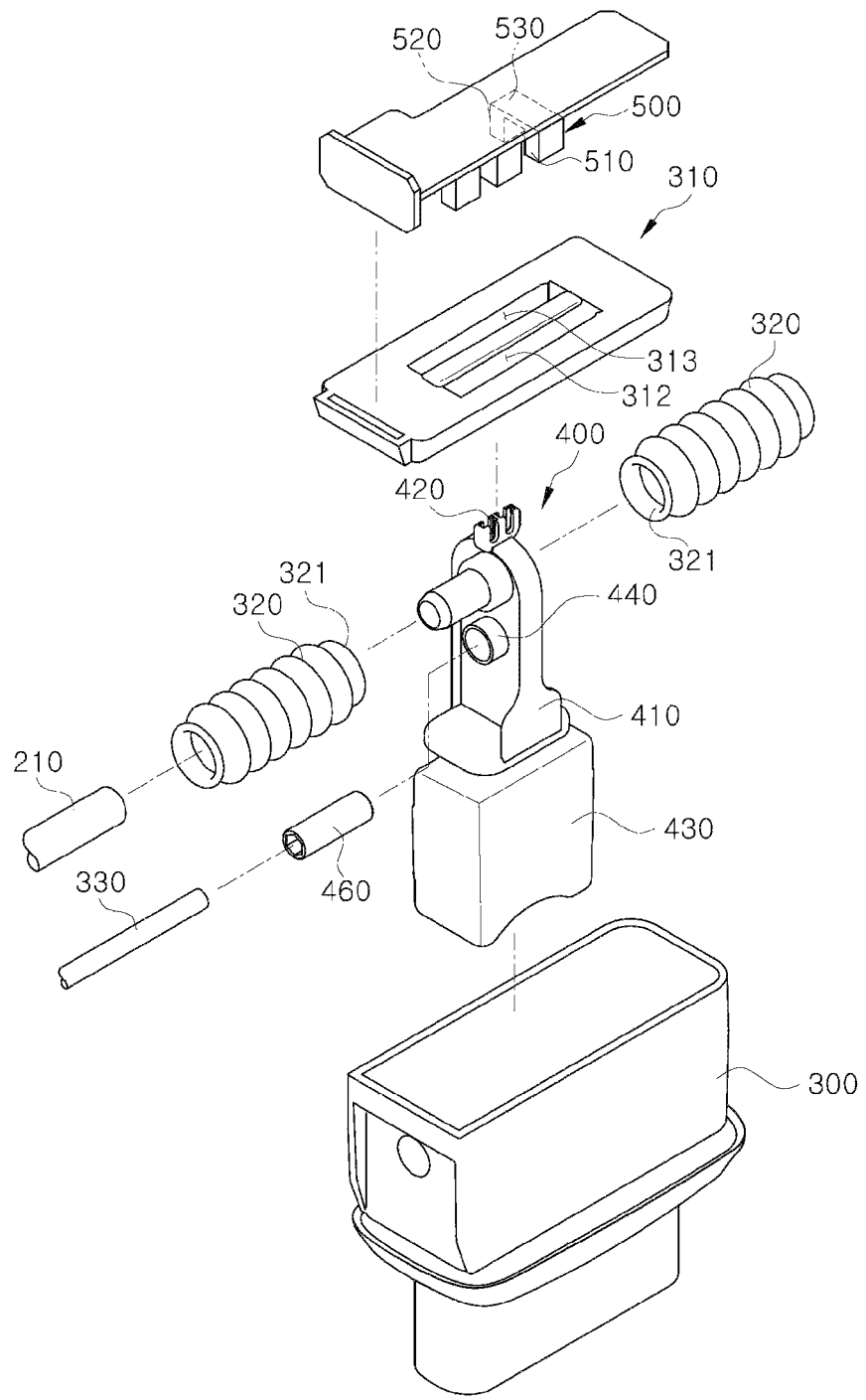
FIG. 2 is an exploded perspective view illustrating a device for generating ultrasonic waves without a handpiece, according to an embodiment of the inventive concept.
Figure 3:
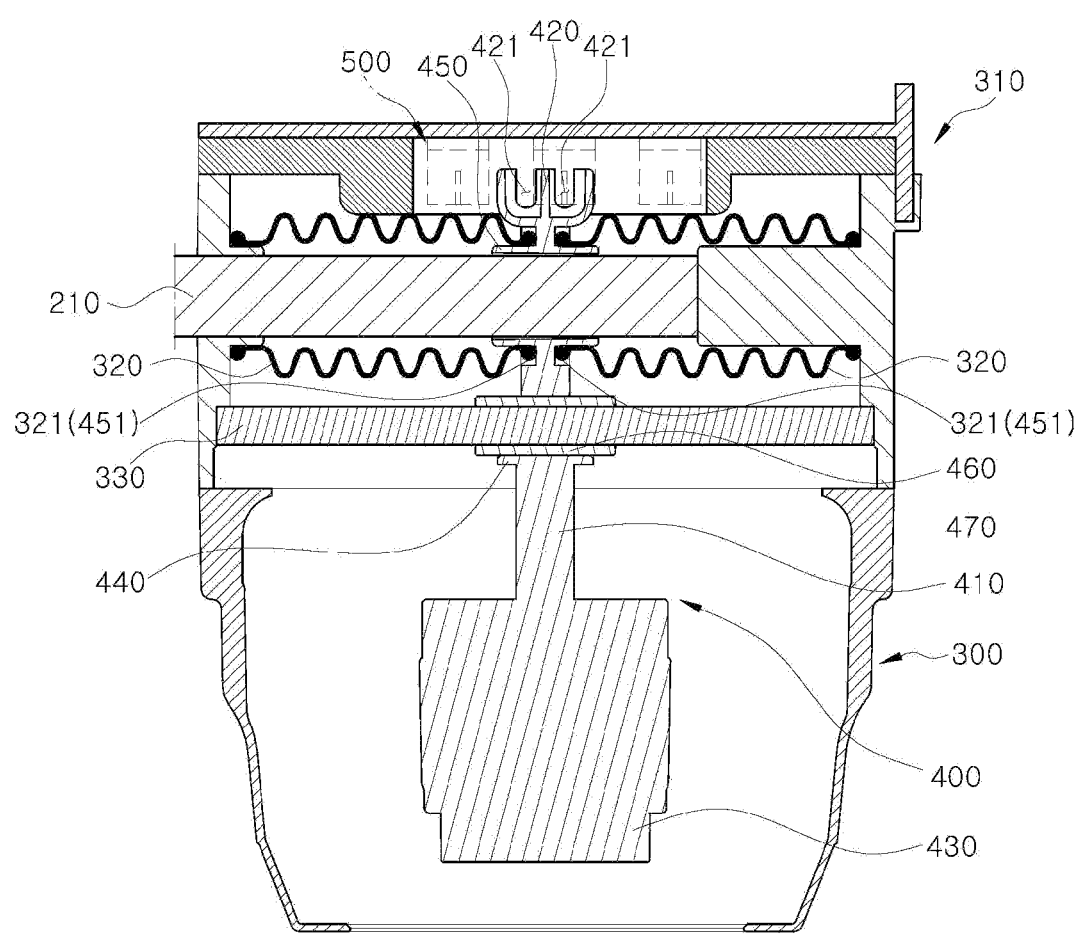
FIG. 3 is a longitudinal-sectional view illustrating a device for generating ultrasonic waves without a handpiece, according to an embodiment of the inventive concept.
Figure 4A:
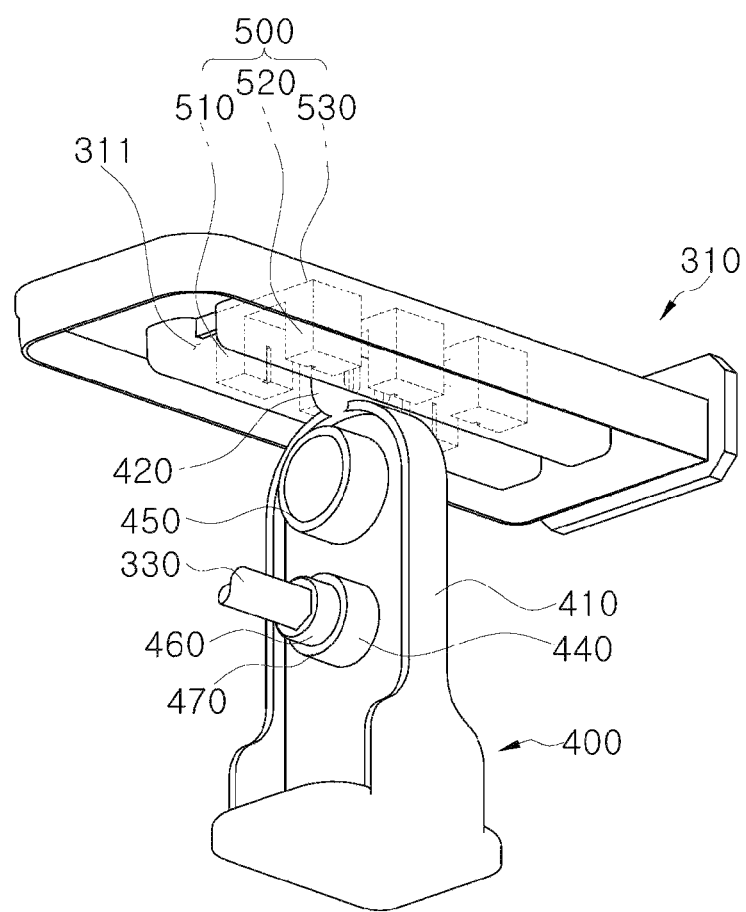
FIG. 4A is a bottom perspective view illustrating a device for generating ultrasonic waves without a handpiece and a cartridge housing, according to an embodiment of the inventive concept.
Figure 4B:
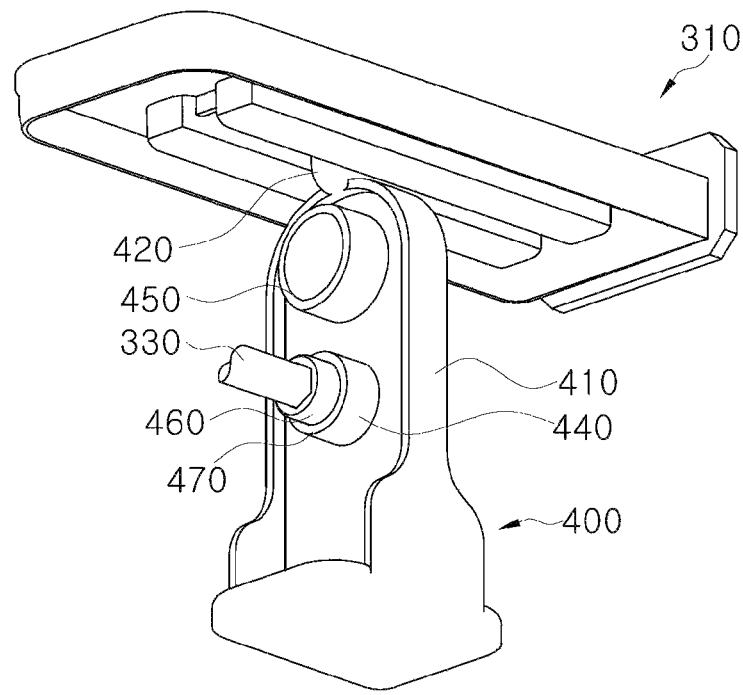
FIG. 4B is a bottom perspective view illustrating a device for generating ultrasonic waves without a handpiece and a cartridge housing, according to an embodiment of the inventive concept.

FIG. 1 is an exploded perspective view illustrating a device for generating ultrasonic waves, according to an embodiment of the inventive concept, FIG. 2 is an exploded perspective view illustrating a device for generating ultrasonic waves without a handpiece, according to an embodiment of the inventive concept, and FIG. 3 is a longitudinal-sectional view illustrating a device for generating ultrasonic waves without a handpiece, according to an embodiment of the inventive concept. FIG. 4A is a bottom perspective view illustrating a device for generating ultrasonic waves without a handpiece and a cartridge housing, according to an embodiment of the inventive concept, and FIG. 4B is a bottom perspective view illustrating a device for generating ultrasonic waves without a handpiece and a cartridge housing, according to an embodiment of the inventive concept.

Figure 5A:
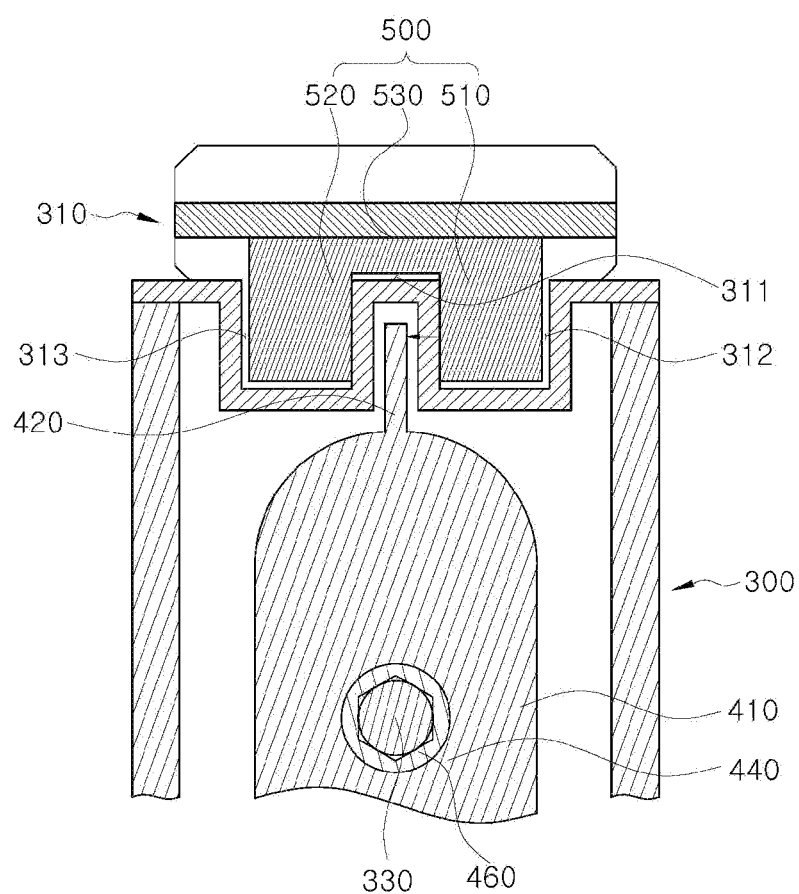
FIGS. 5A, 5B, and 5C are cross-sectional views illustrating a cartridge housing, according to various embodiments of the inventive concept.
Figure 5B:
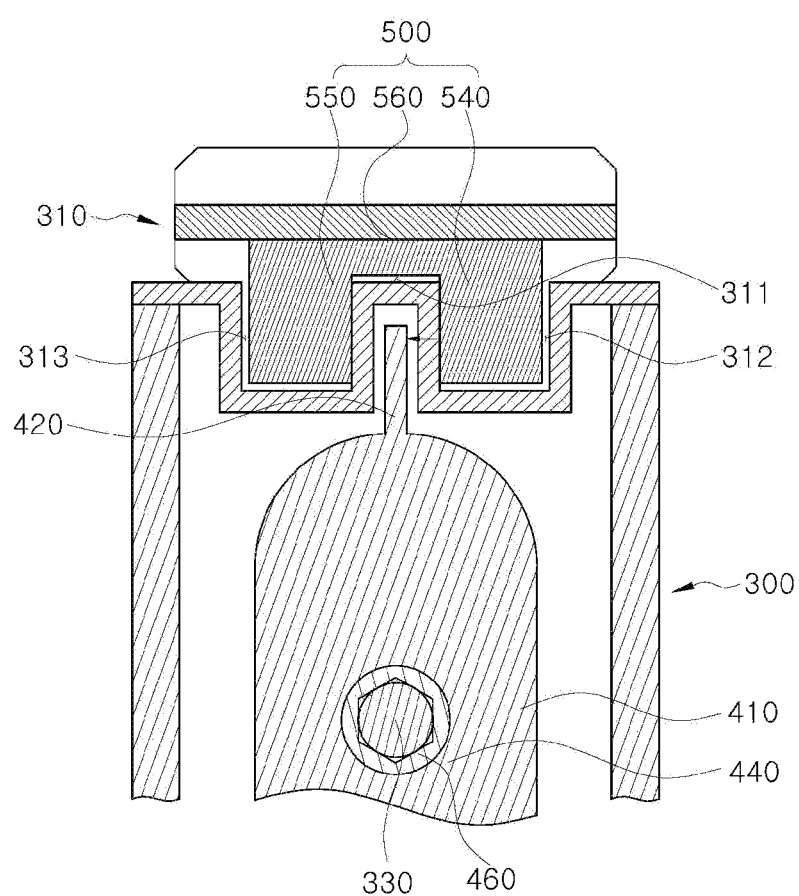
Figure 5C:
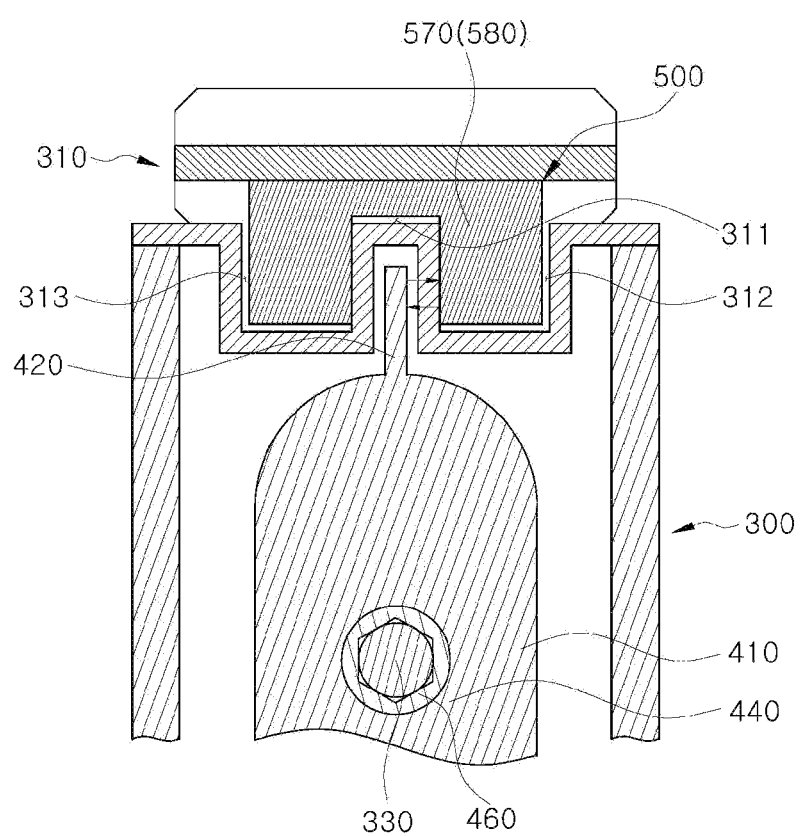
Figure 6:
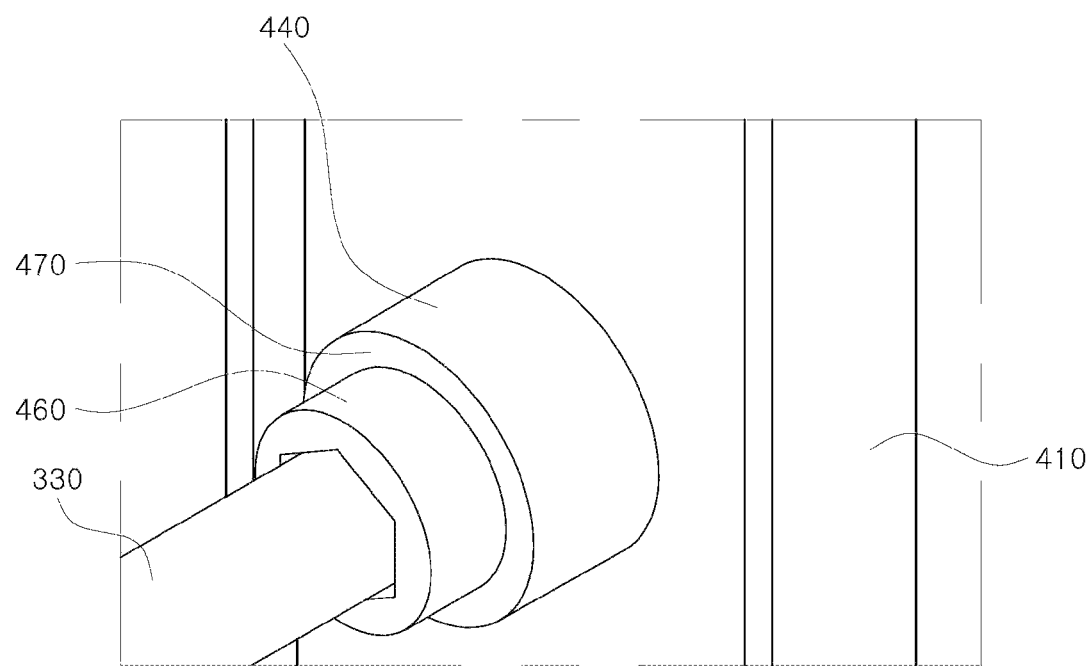
FIG. 6 is a perspective view illustrating a mounter, a bushing, and a guide shaft, according to an embodiment of the inventive concept.

FIGS. 5A, 5B, and 5C are cross-sectional views illustrating a cartridge housing, according to various embodiments of the inventive concept. FIG. 6 is a perspective view illustrating a mounter, a bushing, and a guide shaft, according to an embodiment of the inventive concept.

As illustrated in FIGS. 1 to 6, according to an embodiment of the inventive concept, a device for generating ultrasonic waves includes a handpiece 100, a cartridge housing 300, an ultrasonic wave generating unit 400, and a position sensing unit 500.

Overall, according to an embodiment of the inventive concept, the device for generating the ultrasonic wave senses the position of the ultrasonic wave generating unit 400 received in the cartridge housing 300. For example, the position sensing unit 500 forms a sensing region for sensing a real-time position of the ultrasonic wave generating unit 400 by transmitting a transmission signal to a movement path of the ultrasonic wave generating unit 400.

The handpiece 100 serving as a basic main body may be utilized as a gripper allowing gripping by a user. The cartridge housing 300 to receive the ultrasonic wave generating unit 400 is detachably coupled to one side of the handpiece 100.

Accordingly, the user may grip the handpiece 100, move the handpiece 100 to bring the cartridge housing 300 into close contact with a skin surface, and irradiate a high intensity focused ultrasonic wave from the ultrasonic wave generating unit 400 to a specific depth of a deep skin part, thereby performing an ultrasonic medical treatment.

The handpiece 100 may have a cable which is provided therein and connected to an RF board to apply an RF current to a moving device 200 and the ultrasonic wave generating unit 400. The RF board may be received in the cartridge housing 300, and may intermittently or continuously apply the RF current to a driving device and the ultrasonic wave generating unit 400.

The moving device 200 functions to provide power for moving the ultrasonic wave generating unit 400. The moving device 200 may move the ultrasonic wave generating unit 400 through a main shaft 210 coupled to a mounter 450 of the ultrasonic wave generating unit 400 while passing through the mounter 450. For example, the moving device 200 may include an actuator or a motor to reciprocally move the main shaft 210. Furthermore, the direction for the moving device 200 to move the main shaft 210 may be a longitudinal direction of the handpiece 100 or a longitudinal direction of the cartridge housing 300. In addition, the moving device 200 may be mounted in the handpiece 100 or the cartridge housing 300.

The cartridge housing 300, which is a type of a case to receive the ultrasonic wave generating unit 400, is detachably coupled to the one side of the handpiece 100.

The cartridge housing 300 may, therein, receive a medium for the high intensity focused ultrasonic wave generated from the ultrasonic wave generating unit 400. For example, the medium may be distilled water, deaeration liquid, or silicone, but the inventive concept is not limited thereto.

The ultrasonic wave generating unit 400 is provided to reciprocate in the cartridge housing 300 and to generate the high intensity focused ultrasonic wave. The ultrasonic wave generating unit 400 may include a frame 410, a target member 420, a transducer 430, a slider 440, the mounter 450, and a bushing 460.

In this case, the frame 410, the target member 420, the transducer 430, the slider 440, the mounter 450, and the bushing 460 in the ultrasonic wave generating unit 400 are integrally coupled to each other to move together.

In addition, the ultrasonic wave generating unit 400 may be moved by the moving device 200 which moves the main shaft 210 coupled to the mounter 450 of the ultrasonic wave generating unit 400.

The frame 410 serving as a basic main body may be integrally coupled to the target member 420, the slider 440, and the mounter 450. The target member 420 may be coupled to an upper portion of the frame 410. The transducer 430 may be detachably coupled to a lower portion of the frame 410. In addition, the mounter 450 and the slider 440 may be positioned between the target member 420 and the transducer 430 and coupled to the frame 410 while passing through the frame 410. The mounter 450 may be interposed between the target member 420 and the slider 440, in the frame 410. Meanwhile, the central axial line of the target member 420 and the central axial line of the transducer 430 may be aligned in line with the central axial line of the frame 410. Accordingly, the position sensing unit 500 may calculate the position of the central axial line of the transducer 430, by sensing the position of the central axial line of the target member 420, which is positioned at the sensing region.

The target member 420 is introduced into the sensing region, when the ultrasonic wave generating unit 400 moves. As described above, when the target member 420 is introduced into the sensing region, the target member 420 may block a transmission signal which is transmitted to the sensing region. Accordingly, the position sensing unit 500 may sense the characteristic of the transmission signal blocked by the target member 420, which arrives at the sensing region, to sense the position of the target member 420 in the sensing region, thereby calculating the position of the ultrasonic wave generating unit 400.

The target member 420 may move along a track 311 of a guide plate 310.

The guide plate 310, which covers an upper portion of the cartridge housing 300, has the track 311 formed at the center of the guide plate 310 to guide movement of the target member 420. In this case, the track 311 may be formed in a moving direction of the target member 420. Referring to FIG. 5, the track 311 may be formed in an 'n' shape, when viewed the cross-sectional view of the guide plate 310.

The guide plate 310 may have a first slot 312 and a second slot 313 formed at opposite sides of the guide plate 310, respectively, while interposing the track 311 between the first slot 312 and the second slot 313. A transmission unit 510 and a reception unit 520 of the position sensing unit 500 may be fitted into the first slot 312 and the second slot 313, respectively. Accordingly, the sensing region may be formed between the transmission unit 510 fitted into the first slot 312 and the reception unit 520 fitted into the second slot 313. Referring to FIG. 5, each of the first slot 312 and the second slot 313 may be formed in an 'U' shape, when viewed the cross-sectional view of the guide plate 310.

Furthermore, the first slot 312 and the second slot 313 may be formed in parallel to the track 311. Accordingly, the position of the transmission unit 510 in the first slot 312 may be simply adjusted, as the transmission unit 510 slides in the first slot 312, and the position of the reception unit 520 in the second slot 313 may be simply adjusted, as the reception unit 520 slides in the second slot 313. Accordingly, the position of the sensing region formed between the transmission unit 510 and the reception unit 520 may be simply adjusted.

Meanwhile, the guide plate 310 preferably is made of a material for transmitting light or ultrasonic waves constituting the transmission signal. For example, the guide plate 310 may include a transparent film, but the inventive concept is not specifically limited thereto.

The transducer 430 may receive the RF current from the RF board of the handpiece 100 to generate the high intensity focused ultrasonic wave.

The mounter 450, which is interposed between the target member 420 and the transducer 430, may be coupled to a distal end of the main shaft 210 detachably or integrally. Accordingly, when the moving device 200 moves the main shaft 210, the mounter 450 may be moved together.

For example, the opposite sides of the mounter 450 may be supported by a pair of bellows 320. The pair of bellows 320 may be disposed while interposing the mounter 450 therebetween. For example, one end of the bellows 320 may be detachably coupled to one surface of the mounter 450 in the moving direction, and the other end of the bellows 320 may make contact with the inner surface of the cartridge housing 300.

Accordingly, when the mounter 450 moves, as any one of the pair of bellows 320 is contracted, and the other one of the pair of bellows 320 is expanded, the pair of bellows 320 may support the mounter 450.

Meanwhile, any one of the bellows 320 and the mounter 450 may have an inserting protrusion 321 formed to protrude, and the other one of the bellows 320 and the mounter 450 may have a recess 451 such that the inserting protrusion 321 is detachably coupled to the recess 451. For example, referring to FIG. 3, as the inserting protrusion 321 is formed on one end of the bellows 320, and the recess 451 is formed in an outer circumferential surface of the mounter 450, the inserting protrusion 321 of the bellows 320 may be detachably coupled to the recess 451 of the mounter 450. In more detail, the inserting protrusion 321 of the bellows 320 and the recess 451 of the mounter 450 may be formed in a ring shape.

The slider 440 is interposed between the target member 420 and the transducer 430. The slider 440 may slide along a guide shaft 330 disposed in parallel to the moving direction of the target member 420, in the cartridge housing 300. In this case, opposite ends of the guide shaft 330 may be fixed to opposite surfaces of the cartridge housing 300, and the guide shaft 330 may pass through the slider 440 to guide sliding of the slider 440.

The bushing 460 is provided on an inner circumferential surface of the slider 440. When the slider 440 slides along the guide shaft 330, the bushing 460 serves to reduce abrasion of the slider 440. The bushing 460 may have the form protruding to opposite sides of the slider 440.

Meanwhile, when the slider 440 slides along the guide shaft 330, as friction is caused due to the surface contact between the bushing 460, which is provided on the inner circumferential surface of the slider 440, and the guide shaft 330, the slider 440 may be biased.

To prevent this, the inner circumferential surface of the bushing 460 may have a polygonal shape, for example, a quadrangle, hexagonal, or octagonal shape as illustrated in FIG. 6. However, the inventive concept is not limited to the polygonal shape. More preferably, the inner circumferential surface of the bushing 460 may have the hexagonal shape. Accordingly, when the slider 440 slides along the guide shaft 330, as friction is caused due to the line contact between the polygonal inner surface of the bushing 460 and the guide shaft, the slider 440 may be prevented from being biased.

The position sensing unit 500 may sense the position of the ultrasonic wave generating unit 400 by transmitting a transmission signal to a movement path of the ultrasonic wave generating unit 400. In this case, the transmission signal may be light or ultrasonic waves.

For example, as illustrated in FIG. 5A, the transmission unit 510 and the reception unit 520 may sense the position of the ultrasonic wave generating unit 400 by irradiating light serving as the transmission signal.

The transmission unit 510 and the reception unit 520 may be disposed to be opposed to each other along the movement path of the ultrasonic wave generating unit 400. More preferably, the transmission unit 510 and the reception unit 520 may be disposed to be opposed to each other along the movement path of the target member 420 of the ultrasonic wave generating unit 400. In detail, the transmission unit 510 may be disposed in the moving direction of the target member 420, in the first slot 312. The reception unit 520 may be disposed in the moving direction of the target member 420, in the second slot 313.

In this case, the transmission unit 510 may irradiate light toward the reception unit 520. The transmission unit 510 may include a light emitting device to emit light. In addition, the light may include an infrared ray, an LED light, an ultraviolet ray, a laser beam, and a visible ray, but the inventive concept is not limited thereto.

The reception unit 520 senses the characteristics of light received from the transmission unit 510. The reception unit 520 may include a light receiving unit to receive the light while sensing the characteristic of the light. In this case, the characteristic of the light may be the intensity of the light or the area of the light.

As described above, as the transmission unit 510 irradiates the light to the reception unit 520, and the reception unit 520 senses the characteristic of the light irradiated from the transmission unit 510, the sensing region may be formed between the transmission unit 510 and the reception unit 520 to sense the arrival of the target member 420.

When the target member 420 arrives at the sensing region, the light irradiated by the transmission unit 510 may be blocked by the target member 420, and the reception unit 520 may sense the characteristic of the light, which is changed as the light is blocked by the target member 420. Accordingly, the position of the ultrasonic wave generating unit 400 may be calculated. In more detail, the central axis line of the target member 420 and the central axis line of the transducer 430 may be aligned with the central axis line of the frame 410. In this case, the position sensing unit 500 may calculate the position of the central axis line of the transducer 430 by sensing the position of the central axis line of the target member 420 arrived at the sensing region.

Meanwhile, the reception unit 520 may sense the position, in which the light is blocked by the target member 420, of the sensing region, thereby sensing the position of the target member 420.

In addition, the reception unit 520 may sense a blocking region, in which the light is blocked by the target member 420, of the sensing region, thereby sensing the position of the target member 420.

To improve the sensitivity of the reception unit 520, the target member 420 may have at least one target slit 421 to transmit light. The target slit 421 may be formed in a direction perpendicular to the moving direction of the target member 420. In addition, at least two target slits 421 may be arranged in the moving direction of the target member 420.

Accordingly, while the target member 420 passes through the sensing region, the light irradiated from the transmission unit 510 may pass through the target slit 421 and may arrive at the reception unit 520. The reception unit 520 may sense the real-time position of the target member 420 by tracking the displacement of the light after the light passes through the target slit 421.

Meanwhile, the transmission unit 510 and the reception unit 520 may be formed integrally with each other through a connector 530. The connector 530 may be formed to connect a top surface of the transmission unit 510 to a top surface of the reception unit 520. Accordingly, a user may simultaneously adjust the position of the transmission unit 510 in the first slot 312 and the position of the reception unit 520 in the second slot 313 by moving the transmission unit 510 and the reception unit 520 formed integrally with each other through the connector 530.

For another example, as illustrated in FIG. 5B, a transmission unit 540 and a reception unit 550 may sense the position of the ultrasonic wave generating unit 400 by employing ultrasonic waves as the transmission signal. In addition, the transmission unit 540 and the reception unit 550 may be configured to be separated from each other. Meanwhile, the transmission unit 540 and the reception unit 550 may be connected to each other through a connector 560.

According to this example, the transmission unit 540 and the reception unit 550 are configured by individually employing a transmitting ultrasonic wave sensor and a receiving ultrasonic wave sensor, respectively.

The transmission unit 540 and the reception unit 550 may be provided while interposing the movement path of the target member 420 therebetween. In detail, the transmission unit 540 may be disposed in the moving direction of the target member 420, in the first slot 312, and the reception unit 550 may be disposed in the moving direction of the target member 420, in the second slot 313.

At least one transmission unit 540 may irradiate ultrasonic waves to at least one reception unit 550. In this case, when the target member 420 is positioned between the transmission unit 540 and the reception unit 550, the ultrasonic wave irradiated from the transmission unit 540 is reflected from the target member 420 and thus fails to reach the reception unit 550. In this case, as the position of the ultrasonic wave failing to reach the reception unit 550 is sensed, the position of the target member 420 may be sensed.

For another example, as illustrated in FIG. 5C, a transmission unit 570 and a reception unit 580 may sense the position of the ultrasonic wave generating unit 400 by employing ultrasonic waves as the transmission signal. In addition, the transmission unit 570 and the reception unit 580 may be configured integrally with each other.

According to this example, the transmission unit 570 and the reception unit 580 formed integrally with each other may be arranged in the moving direction of the target member 420, in the first slot 312. In addition, the transmission unit 570 and the reception unit 580 formed integrally with each other may be arranged in the moving direction of the target member 420, in the second slot 313.

At least one transmission unit 570 irradiates ultrasonic waves toward the movement path of the target member 420.

In this case, as the ultrasonic wave irradiated from the transmission unit 570 is reflected from the target member 420 and reaches the reception unit 580, the position of the reception unit 550 may be sensed, thereby sensing the position of the target member 420.

FIG. 7 is a longitudinal sectional view illustrating a moving state of a target member, according to an embodiment of the inventive concept.

Figure 7A:
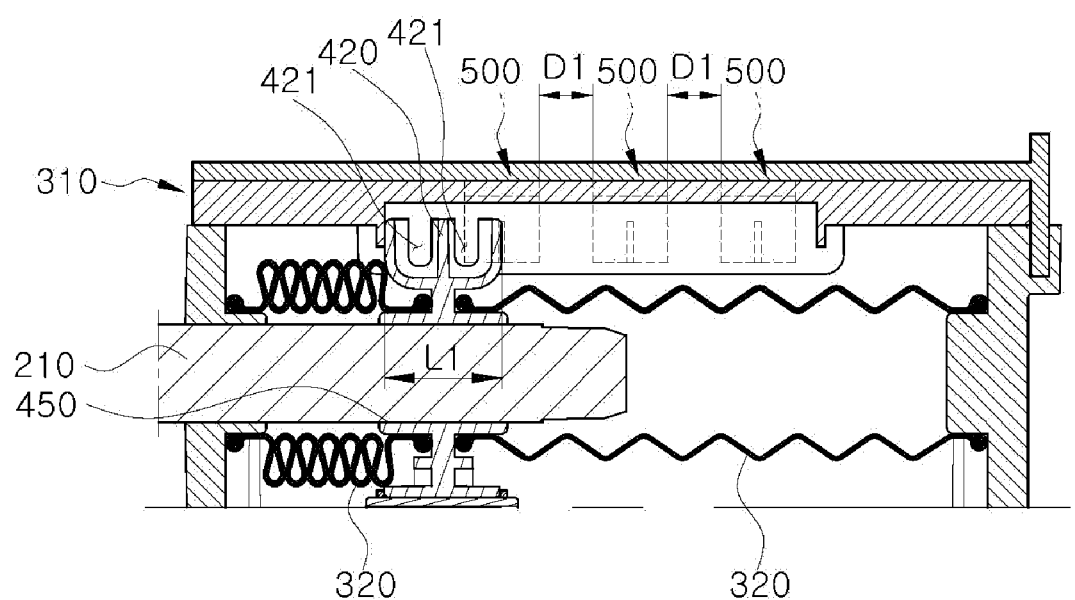
FIGS. 7A-7C are longitudinal-sectional views illustrating a moving state of a target member, according to an embodiment of the inventive concept.
Figure 7B:
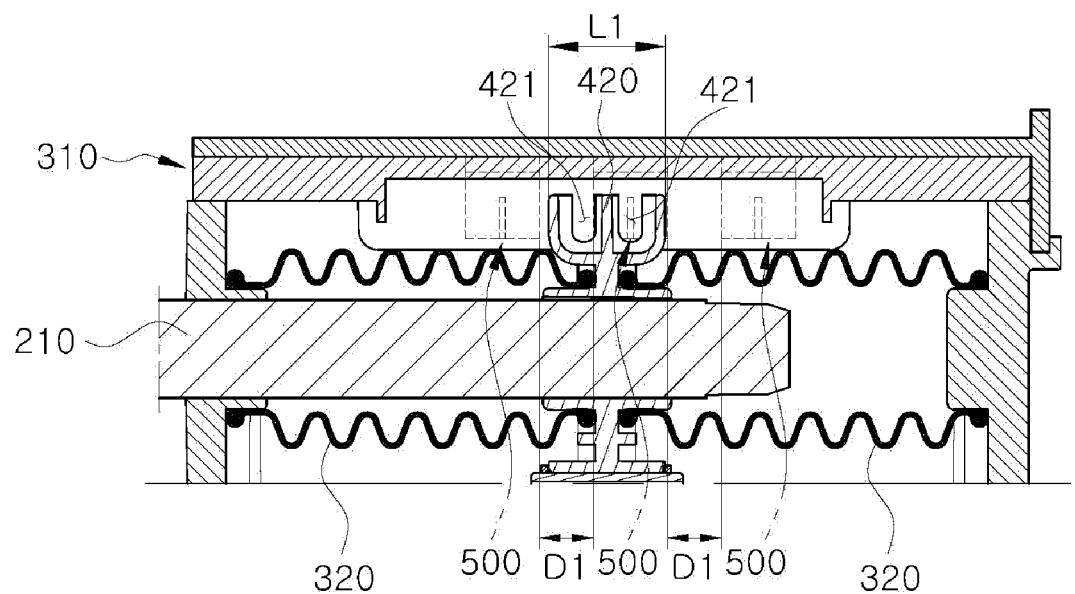
Figure 7C:
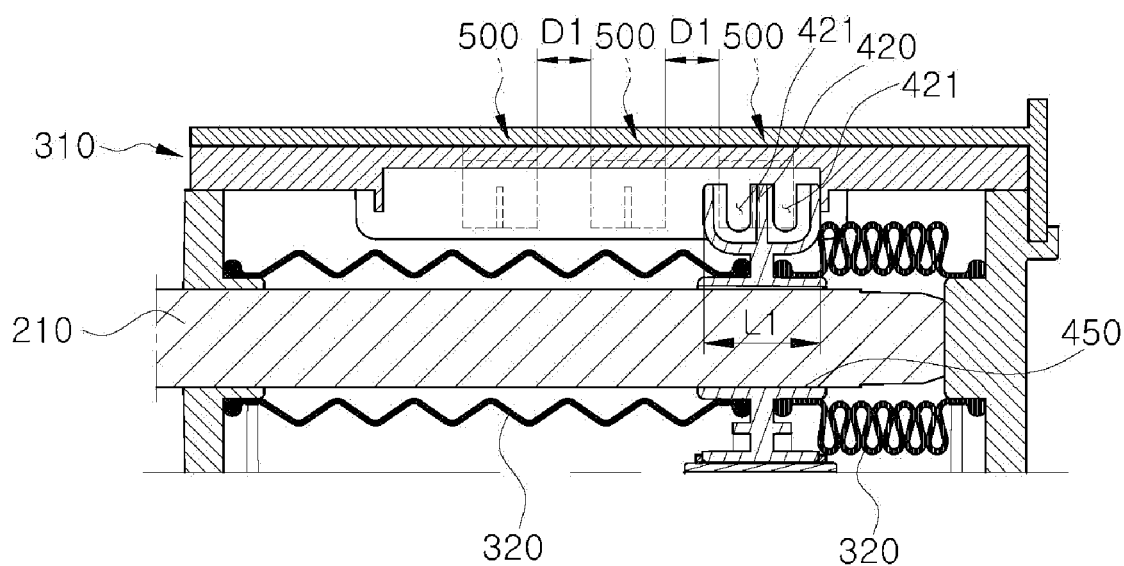

As illustrated in FIGS. 7A-7C, the position sensing unit 500 may include at least one transmission unit 510 and at least one reception unit 520.

The at least one transmission unit 510 and the at least one reception unit 520 may be arranged in a direction parallel to the movement path of the ultrasonic wave generating unit 400, and the sensing region may be formed in every space between the at least one transmission unit 540 and the at least one reception unit 550. In other words, the position sensing unit 500 may form at least one sensing region along the movement path of the target member 420 through the at least one transmission unit 510 and the at least one reception unit 520.

In this case, a distance D1 between two sensing regions adjacent to each other, that is, the distance D1 between two position sensing units 500 adjacent to each other may be shorter than a width L1 in the moving direction of the target member 420. Accordingly, when the target member 420 moves between two sensing regions adjacent to each other, a portion of the target member 420 is positioned in at least one of the two sensing regions adjacent to each other. Accordingly, the position sensing unit 500 may sense the real-time position of the target member 420 through the portion of the target member 420 positioned in at least one of two sensing regions adjacent to each other.

Meanwhile, according to an embodiment of the inventive concept, the cartridge for generating the ultrasonic wave has the cartridge housing 300, the ultrasonic wave generating unit 400, and the position sensing unit 500, without the handpiece 100 and the moving device 200 in the device for generating the ultrasonic wave. Hereinafter, the details thereof will be omitted.

In addition, according to an embodiment of the inventive concept, the handpiece for generating the ultrasonic wave may include the cartridge housing 300 detachably coupled to the handpiece 100, and the ultrasonic wave generating unit 400 provided to reciprocate in the cartridge housing 300. In addition, the position sensing unit 500 may be provided in the handpiece 100 to sense the real-time position of the ultrasonic wave generating unit 400.

According to the inventive concept, the cartridge for generating the ultrasonic wave and the device for generating the ultrasonic wave including the same may form the sensing region to sense the real-time position of the ultrasonic wave generating unit 400 by transmitting the transmission signal to the movement path of the ultrasonic wave generating unit 400, thereby sensing the position of the ultrasonic wave generating unit 400 in real time.

Meanwhile, according to an embodiment of the inventive concept, a skin treatment method using the cartridge or the handpiece for generating the ultrasonic wave includes: performing skin treatment, as an ultrasonic wave generating unit moves along a specific path or stops at a specific point in the cartridge housing by a control unit; and detecting the real-time position of the ultrasonic wave generating unit by transmitting the transmission signal to the movement path of the ultrasonic wave generating unit 400 by the control unit. In this case, the control unit may be an individual control device, such as a micro-computer, but the inventive concept is not limited thereto.

According to an embodiment of the inventive concept, in the cartridge, the device, and the handpiece for generating ultrasonic waves, and the method for sensing the position of the ultrasonic wave generating unit, as the transmission signal is transmitted to the movement path of the ultrasonic wave generating unit through the position sensing unit to form the sensing region for sensing the real-time position of the ultrasonic wave generating unit, thereby sensing the position of the ultrasonic wave generating unit in real time.

Effects to be solved by the inventive concept are not limited to the effects mentioned above, and other effects not mentioned will be clearly understood by those skilled in the art from the following description.

Although an embodiment of the inventive concept are described with reference to the accompanying drawings, it will be understood by those skilled in the art to which the inventive concept pertains that the inventive concept can be carried out in other detailed forms without changing the scope and spirit or the essential features of the inventive concept. Therefore, the embodiments described above are provided by way of example in all aspects, and should be construed not to be restrictive.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A cartridge for generating ultrasonic waves, the cartridge comprising:
   a cartridge housing;
   a guide shaft disposed in the cartridge housing;
   an ultrasonic wave generator provided in the cartridge housing, wherein the ultrasonic wave generator is configured to reciprocate; and
   a position sensor configured to sense a real-time position of the ultrasonic wave generator by transmitting at least one transmission signal to a movement path of the ultrasonic wave generator;
   wherein the ultrasonic wave generator includes:
      a slider configured to slide along the guide shaft as the guide shaft passes through the slider; and
      a bushing provided on an inner circumferential surface of the slider.

2. The cartridge of claim 1, wherein the position sensor includes:
   at least one transmitter configured to transmit the at least one transmission signal; and
   at least one receiver configured to receive the at least one transmission signal.

3. The cartridge of claim 2, wherein the position sensor further includes:
   at least one reflector configured to reflect the at least one transmission signal.

4. The cartridge of claim 3, wherein the ultrasonic wave generator includes:
   a target member configured to block a respective transmission signal from passing between the at least one transmitter and the at least one receiver while the ultrasonic wave generator is moving; and
   a transducer coupled to the target member.

5. The cartridge of claim 4, wherein at least one sensing region is formed between the at least one transmitter and the at least one receiver.

6. The cartridge of claim 4, wherein the target member has at least one target slit configured to allow a respective transmission signal to pass through the at least one target slit.

7. The cartridge of claim 4, further comprising:
   a pair of bellows in the cartridge housing, wherein the pair of bellows are spaced apart from each other in the moving direction of the target member;
   wherein the ultrasonic wave generator further includes a mounter interposed between the pair of bellows.

8. The cartridge of claim 7, wherein an inserting protrusion is formed to protrude from one of the bellows and the mounter; and
   wherein a recess is formed in the other one of the bellows and the mounter, such that the inserting protrusion is detachably coupled to the recess.

9. The cartridge of claim 7, wherein the position sensor comprises multiple transmitters and multiple receivers;
   wherein multiple respective sensing regions are formed between the multiple transmitters and multiple receivers; and
   wherein a distance between two respective adjacent sensing regions is less than a top width of the mounter.

10. The cartridge of claim 2, wherein the at least one transmitter and the at least one receiver are disposed integrally with each other, aligned in line with each other, or disposed to be opposed to each other.

11. The cartridge of claim 2, wherein the at least one transmitter and the at least one receiver are aligned in line with each other or disposed to be opposed to each other along the movement path of the ultrasonic wave generator.

12. The cartridge of claim 1, wherein the bushing has a polygonal shape.

13. The cartridge of claim 1, wherein the cartridge is mounted in a handpiece.

14. A handpiece for generating ultrasonic waves, the handpiece comprising:
    a cartridge housing detachably provided in the handpiece;
    a guide shaft disposed in the cartridge housing;
    an ultrasonic wave generator configured to reciprocate in the cartridge housing, and
    a position sensor configured to sense a real-time position of the ultrasonic wave generator;
    wherein the ultrasonic wave generator includes:
       a slider configured to slide along the guide shaft as the guide shaft passes through the slider; and
       a bushing provided on an inner circumferential surface of the slider.

15. A method, comprising:
    reciprocating an ultrasonic wave generator in a cartridge housing along a movement path, wherein reciprocation of the ultrasonic wave generator in the cartridge housing is based on a slider of the ultrasonic wave generator sliding along a guide shaft disposed in the cartridge housing as the guide shaft passes through the slider, and wherein the ultrasonic wave generator comprises a bushing provided on an inner circumferential surface of the slider; and
    sensing, by a position sensor, a real-time position of the ultrasonic wave generator, wherein sensing the real-time position of the ultrasonic wave generator comprises:
       transmitting a transmission signal to the movement path of the ultrasonic wave generator; and
       detecting the real-time position of the ultrasonic wave generator based on the transmission signal.

16. The method of claim 15, wherein the position sensor includes:
    a transmitter configured to transmit the transmission signal; and
    a receiver configured to receive the transmission signal.

17. The method of claim 16, wherein the position sensor further includes:
    a reflector configured to reflect the transmission signal.

18. The method of claim 17, wherein the ultrasonic wave generator includes:

a target member configured to block a respective transmission signal from passing between the transmitter and the receiver while the ultrasonic wave generator is moving; and
a transducer coupled to the target member.

19. The method of claim 18, wherein a sensing region is formed between the transmitter and the receiver.

* * * * *